(12) United States Patent
Wang et al.

(10) Patent No.: US 8,216,225 B2
(45) Date of Patent: Jul. 10, 2012

(54) IRRIGATED ABLATION ELECTRODE ASSEMBLY HAVING A POLYGONAL ELECTRODE

(75) Inventors: Huisun Wang, Maple Grove, MN (US); Harry A. Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 977 days.

(21) Appl. No.: 11/962,617

(22) Filed: Dec. 21, 2007

(65) Prior Publication Data

US 2009/0163912 A1    Jun. 25, 2009

(51) Int. Cl.
*A61B 18/14* (2006.01)
*A61N 1/00* (2006.01)

(52) U.S. Cl. .......................... 606/41; 607/115

(58) Field of Classification Search ............... 606/32–34, 606/40–42, 49; 600/372–375, 377–381, 600/393
See application file for complete search history.

(56) References Cited

U.S. PATENT DOCUMENTS

| | | | |
|---|---|---|---|
| 5,056,517 A | 10/1991 | Fenici | |
| 5,230,349 A | 7/1993 | Langberg | |
| 5,334,193 A | 8/1994 | Nardella | |
| 5,348,554 A | 9/1994 | Imran et al. | |
| 5,423,811 A | 6/1995 | Imran et al. | |
| 5,433,708 A * | 7/1995 | Nichols et al. | 604/113 |
| 5,462,521 A | 10/1995 | Brucker et al. | |
| 5,545,161 A | 8/1996 | Imran | |
| 5,643,197 A | 7/1997 | Brucker et al. | |
| 5,658,278 A | 8/1997 | Imran et al. | |
| 5,697,927 A | 12/1997 | Imran et al. | |
| 5,792,140 A | 8/1998 | Tu et al. | |
| 5,843,152 A | 12/1998 | Tu et al. | |
| 5,893,884 A | 4/1999 | Tu | |
| 5,913,856 A | 6/1999 | Chia et al. | |
| 5,919,188 A | 7/1999 | Shearon et al. | |
| 6,015,407 A | 1/2000 | Rieb et al. | |

(Continued)

FOREIGN PATENT DOCUMENTS

WO    2005/048858 A1    6/2005

(Continued)

OTHER PUBLICATIONS

Wittkampf, et al., Radiofrequency Ablation with a Cooled Porous Electrode Catheter, JACC vol. 11, No. 2, Feb. 1988: 17A Abstracts.

(Continued)

*Primary Examiner* — Michael Peffley
*Assistant Examiner* — Thomas Giuliani
(74) *Attorney, Agent, or Firm* — Dykema Gossett PLLC (57) ABSTRACT

An irrigated ablation electrode assembly includes a substantially polygonal shaped electrode. The electrode assembly includes a proximal portion having an outer body portion including an outer distal end surface and an inner cavity within the outer body portion. The proximal portion of the electrode assembly further includes at least one passageway for fluid that extends from the inner cavity of the proximal member to the outer distal end surface of the proximal member. The electrode assembly further includes a distal portion defined by a substantially polygonal shaped body. Irrigation fluid flows from the inner cavity of the proximal portion through the passageway and out an orifice provided on the outer distal end surface of the proximal portion. The fluid that exits the passageway flows substantially parallel to the distal portion, therein improving the irrigation of the electrode.

27 Claims, 5 Drawing Sheets

U.S. PATENT DOCUMENTS

| | | | |
|---|---|---|---|
| 6,017,338 | A | 1/2000 | Brucker et al. |
| 6,120,476 | A | 9/2000 | Fung et al. |
| 6,171,275 | B1 | 1/2001 | Webster, Jr. |
| 6,217,576 | B1 | 4/2001 | Tu et al. |
| 6,602,242 | B1 | 8/2003 | Fung et al. |
| 6,611,699 | B2 * | 8/2003 | Messing .................. 600/372 |
| 6,855,143 | B2 * | 2/2005 | Davison et al. ............ 606/41 |
| 6,942,661 | B2 | 9/2005 | Swanson |
| 7,166,105 | B2 | 1/2007 | Mulier et al. |
| 7,331,957 | B2 * | 2/2008 | Woloszko et al. .......... 606/41 |
| 7,628,788 | B2 * | 12/2009 | Datta ........................ 606/41 |
| 7,815,635 | B2 * | 10/2010 | Wittkampf et al. ........ 606/41 |
| 2002/0198520 | A1 * | 12/2002 | Coen et al. ................ 606/41 |
| 2005/0177151 | A1 | 8/2005 | Coen et al. |
| 2007/0156131 | A1 | 7/2007 | Datta |
| 2010/0152727 | A1 * | 6/2010 | Gibson et al. ............. 606/41 |

FOREIGN PATENT DOCUMENTS

WO  2005/112814 A1  12/2005

OTHER PUBLICATIONS

Wittkampf, et al., Saline-Irrigated Radiofrequency Ablation Electrode with External Cooling, Journal of Cardiovascular Electrophysiology, vol. 16, No. 3, Mar. 2005.

International Search Report and Written Opinion for PCT/US2008/083910 mailed Jan. 15, 2009.

Thomas, et al., A Comparison Of Open Irrigated And Non-Irrigated Tip Catheter Ablation For Pulmonary Vein Isolation, Europace 6:330-335 (2004).

* cited by examiner

IRRIGATED ABLATION ELECTRODE ASSEMBLY HAVING A POLYGONAL ELECTRODE

BACKGROUND OF THE INVENTION a. Field of the Invention

The instant invention relates to ablation electrodes and/or electrode assemblies. The present invention further relates to ablation electrodes and/or assemblies having a mechanism for irrigating targeted areas. The present invention further relates to irrigated ablation electrodes and/or assemblies that allow for a parallel irrigation flow path through the use of polygonal shaped electrodes.

b. Background Art

Electrophysiology catheters have been used for an ever-growing number of procedures. For example, catheters have been used for diagnostic, therapeutic, and ablative procedures, to name just a few examples. Typically, a catheter is manipulated through the patient's vasculature and to the intended site, for example, a site within the patient's heart, and carries one or more electrodes, which may be used for ablation, diagnosis, or other treatments.

There are a number of methods used for ablation of desired areas, including for example, radiofrequency (RF) ablation. RF ablation is accomplished by transmission of radiofrequency energy to a desired target area through an electrode assembly to ablate tissue at the target site. Because RF ablation may generate significant heat, which if not controlled can result in excessive tissue damage, such as steam pop, tissue charring, and the like, it is desirable to include a mechanism to irrigate the target area and the device with biocompatible fluids, such as saline solution. The use of irrigated ablation catheters can also prevent the formation of soft thrombus and/or blood coagulation.

Typically, there are two classes of irrigated electrode catheters, open and closed irrigation catheters. Closed ablation catheters usually circulate a cooling fluid within the inner cavity of the electrode. Open ablation catheters typically deliver the cooling fluid through open outlets or openings on the surface of the electrode. Open ablation catheters use the inner cavity of the electrode, or distal member, as a manifold to distribute saline solution, or other irrigation fluids known to those skilled in the art, to one or more passageways that lead to openings/outlets provided on the surface of the electrode. The saline thus flows directly through the outlets of the passageways onto the distal electrode member. This direct flow of fluid through the electrode tip lowers the temperature of the tip during operation, rendering accurate monitoring and control of the ablative process more difficult. Accordingly, it is desirable to have a method that allows for cooling of the electrode while having accurate monitoring and control of the ablative process.

The irrigation of electrodes, especially those of longer length (i.e., for example, over 3 mm), have an increased likelihood of developing thrombus caused by protein aggregation and blood coagulation, due to angled irrigation flow away from the electrode tip. Moreover, as the length of the electrode increases, the angled fluid passageways provided by an electrode assembly, are less effective since the fluid is directed away from the electrode instead of along the body of the electrode to effectively cool the electrode and adequately irrigate in order to prevent the development of thrombus. Overall, open flush irrigated ablation catheters may improve the safety of RF catheter ablation by preventing protein aggregation and blood coagulation.

BRIEF SUMMARY OF THE INVENTION

The present invention relates to ablation electrode assemblies. The present invention further relates to an irrigated ablation electrode assembly that includes a substantially polygonal shaped electrode. It is desirable to have an irrigated ablation catheter which aids in providing parallel irrigation fluid flow along the body of the electrode in order to cool the electrode tip effectively. Moreover, the positioning of the irrigation/fluid passageways allows fluid to flow in close proximity to the electrode body.

The present invention relates to an irrigated ablation electrode assembly. The electrode assembly includes a proximal member having an outer body portion including an outer distal end surface and an inner cavity within the outer body portion. The proximal member of the electrode assembly further includes at least one passageway for fluid. The passageway extends from the inner cavity of the proximal member to the outer distal end surface of the proximal member. The electrode assembly further includes a distal member. The distal member is defined by a substantially polygonal shaped body. The polygonal shaped body of the distal member is defined by a longitudinal axis and a radial substantially polygonal cross-section. Irrigation fluid flows from the inner cavity of the proximal member through the passageway and out an orifice provided on the outer distal end surface of the proximal member. The fluid that exits out of the passageways flows substantially parallel to the body of the distal member, therein improving or optimizing the irrigation of the substantially polygonal shaped electrode.

The present invention further relates to an ablation catheter system including an irrigated ablation electrode assembly connected to a catheter shaft, therein forming an irrigated catheter assembly connected to an energy source and a fluid source.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant invention relates to irrigated ablation electrode assemblies and to methods of using the irrigated ablation electrode assemblies in connection with catheter assemblies. For purposes of this description, similar aspects among the various embodiments described herein will be referred to by the same reference number. As will be appreciated, however, the structure of the various aspects may be different among the various embodiments.

Figure 1:
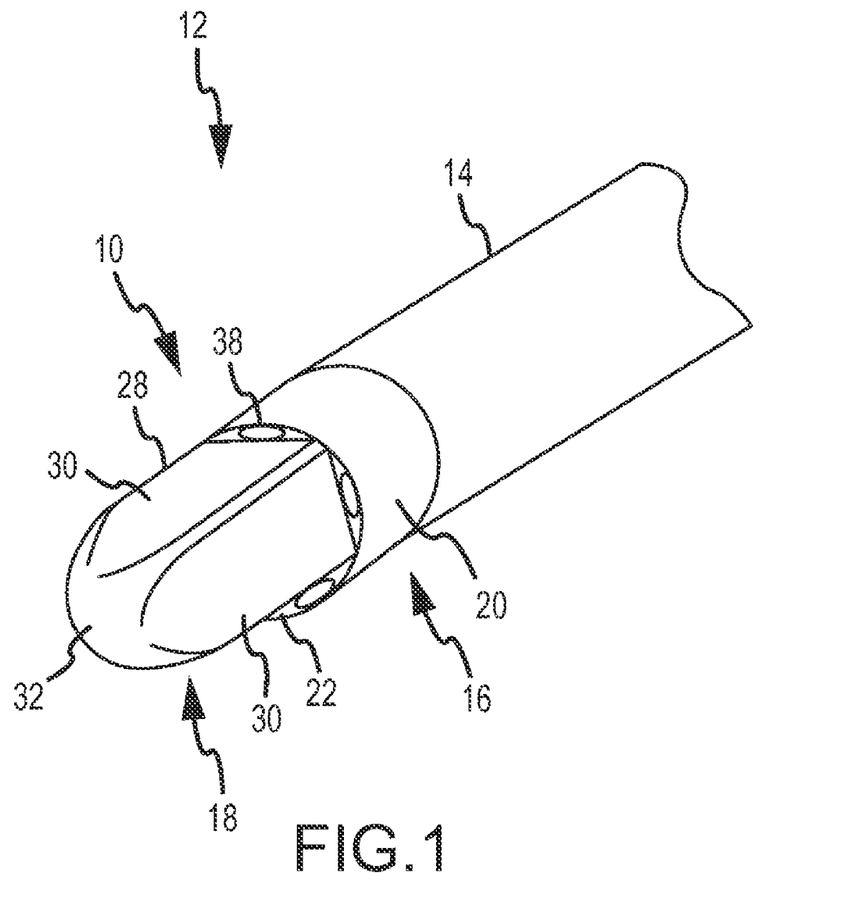
FIG. 1 is an isometric view of an irrigated ablation electrode assembly connected to a catheter shaft in accordance with an embodiment of the present invention.

As generally shown in the embodiment illustrated in FIG. 1, the ablation electrode assembly 10 may comprise part of an irrigated ablation catheter assembly 12. The present embodiments describe RF ablation electrodes and assemblies, but it is contemplated that the present invention is equally applicable to any number of other ablation electrodes and assemblies where the temperature of the device and the targeted tissue area may be factors during the procedure. FIGS. 2-4F, discussed in more detail below, illustrate ablation electrode assemblies 10 according to alternate embodiments of the present invention.

In accordance with an embodiment, FIG. 1 is an isometric view of irrigated ablation electrode assembly 10 connected to a catheter shaft 14 as part of irrigated ablation catheter assembly 12. Catheter assembly 12 further includes at least one fluid delivery tube (not shown) for supplying fluid to electrode assembly 10.

Electrode assembly 10 is generally defined by a proximal member 16 and a distal member 18. Proximal member 16 may also be referred to as a "proximal portion." Similarly, distal member 18 may also be referred to as a "distal portion." For some embodiments, electrode assembly 10 may be designed and configured to comprise a single unitary electrode assembly 10 that includes a proximal portion and a distal portion. In other embodiments, electrode assembly may comprise a multi-component electrode assembly 10 having separately-formed proximal and distal portions.

Figure 2A:
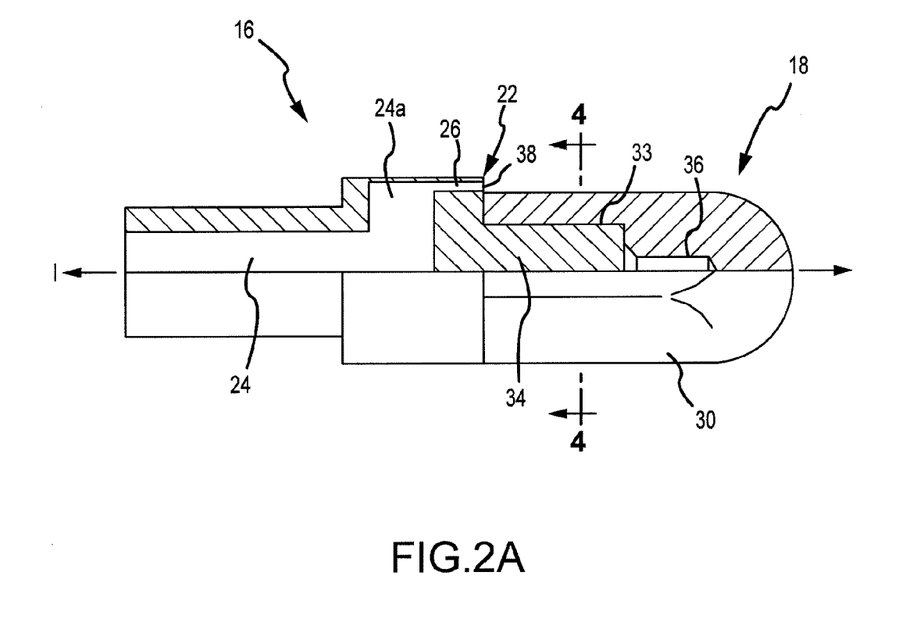
FIG. 2A is a partial cross-sectional side view of the irrigated ablation electrode assembly according to another embodiment of the present invention.
Figure 2B:
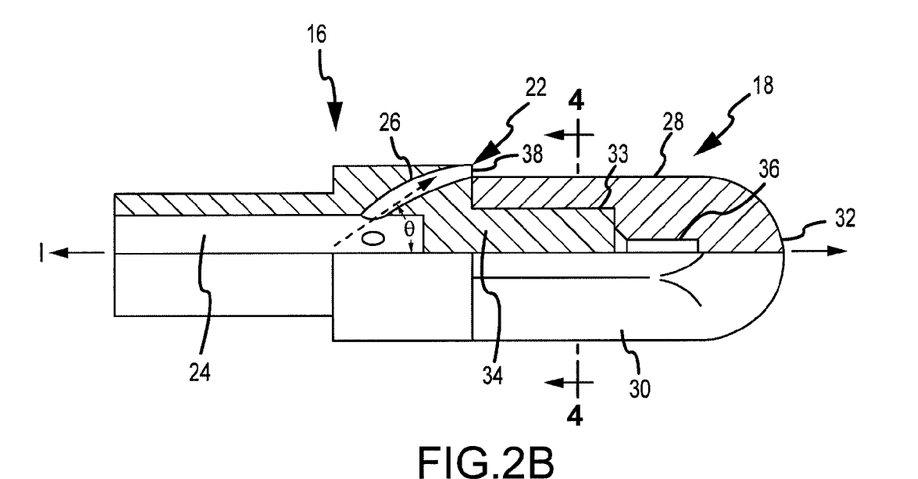
FIG. 2B is a partial cross-sectional side view of the irrigated ablation electrode assembly according to another embodiment of the present invention

As shown in FIGS. 1 and 2, proximal member 16 includes an outer body portion 20 having an outer distal end surface 22. Proximal member 16 further includes an inner cavity 24 that may be coupled to or is in fluid communication with the fluid delivery tube of catheter assembly 12. Proximal member 16 further includes at least one fluid or irrigation passageway 26 that extends from inner cavity 24 to outer distal end surface 22 of proximal member 16. Distal member 18 may be a substantially polygonal shaped body 28 that is distally coupled to/or connected with proximal member 16 to form electrode assembly 10. The substantially polygonal shaped body 28 includes of a number of sides 30 that are oriented together to form various polygonal shapes, such as, for example, a square, a pentagon, a hexagon, an octagon, or any other type of substantially polygonal shape. Although a polygonal shape is traditionally comprised of at least three flat sides, the present invention contemplates a substantially polygonal shaped body that is comprised of at least three sides that may be a combination of flat and curved portions. Accordingly polygonal shaped body 28 is defined by a longitudinal axis (l) and includes a substantially radial polygonal cross-section, as further described in FIGS. 4A-4F. Distal member 18 may further include a rounded (e.g., partially spherical or hemispherical) distal end 32.

Proximal member 16 is generally comprised of a thermally nonconductive or reduced thermally conductive material that serves to insulate the fluid from the remaining portions of electrode assembly 10, in particular, for example, distal member 18. Moreover, proximal member 16 may comprise an electrically nonconductive material. Proximal member 16 is lower in thermal conductivity than distal member 18. In an embodiment, proximal member 16 is made from a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. One reduced thermally conductive material may include polyether ether ketone ("PEEK"). Further examples of reduced thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

Although not shown, proximal member 16 may be configured to receive a fluid delivery tube carried within catheter assembly 12. Moreover, proximal member 16 may include a plurality of passageways 26. Proximal member 16, also referred to as a manifold, distributes fluid throughout and along the outer surface of electrode assembly 10, through the use of passageways 26. In particular, passageways 26 extend from inner cavity 24 axially toward the outer distal end surface 22 of proximal member 16. In an embodiment, passageways 26 may be parallel to the respective outer distal end surfaces 22 of proximal member 16. In an embodiment, passageways 26 may be angled towards outer distal end surface 22 of proximal member 16. More specifically, passageways 26 are either straight or curved towards outer distal end surface 22 of proximal member 16. In an embodiment, a plurality of passageways 26 are substantially equally distributed around proximal member 16 to provide substantially equal distribution of fluid to the targeted tissue area and/or the outside of electrode assembly 10. Proximal member 16 may be configured to provide a single, annular passageway 26, or a number of individual passageways 26 equally distributed around the proximal member 16. Moreover, the passageways 26 may be generally tubular and may have a constant diameter along the length of the passageway. As shown in various Figures, passageways 26 may be substantially oval-shaped, therein providing a substantially oval cross-section and exit orifice. The oval-shaped passageways 26 may increase the flow of fluid surrounding distal member 18 as compared to circular passageways of a smaller cross-section. Alternate configurations of passageways having various diameters along all or portions of the length of the passageways may be used.

As shown in FIG. 2A, at least one passageway 26 may extend towards distal member 18, in particular to outer distal end surface 22 of proximal member 16, parallel to or at least substantially parallel to distal member 18, and more particularly, parallel to the central longitudinal axis (l) of electrode assembly 10. In an embodiment, inner cavity 24 may further include a distal portion 24a that extends into outer body portion 20 of proximal member 16, such that distal portion 24 provides fluid to at least one passageway 26 that is substantially parallel with distal member 18. Accordingly, passageways 26 are provided along the same longitudinal axis as orifice or outlet 38 of passageway 26 provided on outer distal end surface 22 of proximal member 16. This embodiment allows for increased parallel fluid flow directly from inner cavity 24 through distal portion 24a and into passageways 26 therein exiting orifice 38 and substantially flowing along sides 30 of distal member 18.

As shown in FIG. 2B, at least one passageway 26 may extend towards distal member 18, in particular to outer distal end surface 22 of proximal member 16, at an angle (Θ) less than 90 degrees from the central longitudinal axis (l) of electrode assembly 10. In an embodiment, passageways 26 extends at an angle (Θ) between about 0 to about 45 degrees, and for some embodiments, between about 0 to about 25 degrees. Moreover, passageways 26 may be angled by varying degrees depending on the design of electrode assembly 10, such as, for example, the varying lengths of distal member 18 and the overall diameter of electrode assembly 10. Alternate positions and angles of the passageway(s) 26 may be provided in alternate embodiments of electrode assembly 10 as recognized by those of ordinary skill in the art.

Distal member 18 is generally comprised of any electrically, and potentially thermally, conductive material known to those of ordinary skill in the art for delivery of ablative energy to target tissue areas. Examples of electrically conductive material include gold, platinum, iridium, palladium, stainless steel, and any mixtures thereof. In particular, a combination of platinum and iridium may be used in various combinations.

As seen in FIGS. 2A and 2B, cavity 33 may be provided within distal member 18 and is generally configured to receive portion 34 of proximal member 16 to ultimately form electrode assembly 10. Electrode assembly 10 is therein coupled to catheter shaft 14 (as seen in FIG. 1) to form an embodiment of a catheter assembly 12. Alternate embodiments may be provided wherein the electrode assembly is comprised of multiple members that connect or fit together to form the electrode. Various materials may be used in the formation of such electrodes, including a combination of electrically conductive materials and materials that are less thermally conductive. Moreover, each of these components may be coupled or connected together through a number of methods known in the art, including but not limited to, the use of adhesive, bonding, snap fit configurations, locking mechanisms and any other types of coupling or connecting methods available to one of ordinary skill in the art.

Distal member 18 may be further provided with a cavity 36 for receiving a thermal sensor (not shown). Additional components, such as a power wire, a sensing wire or other types of components may be provided within distal member 18 or throughout electrode assembly 10 to enhance the overall performance and function of electrode assembly 10.

Figure 3:
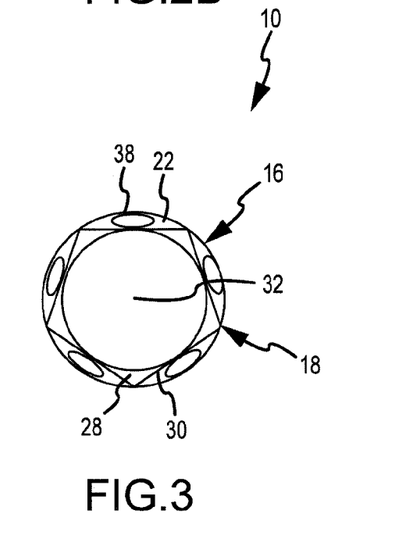
FIG. 3 is a distal end view of the irrigated ablation electrode assembly in an alternate embodiment as shown in FIGS. 2A and 2B.

As shown in FIG. 3, which provides a distal end view of an embodiment of the present invention, distal member 18 includes five sides 30 therein forming a pentagon polygonal body shape. Outer distal end surface 22 of proximal member 16 is shown proximate to distal member 18 and provides a surface for the outlet or orifice 38 for passageway 26, such that fluid flows out orifice 38 of passageway 26 and onto the pentagon shaped body 28 formed by sides 30. In order to enhance fluid flow, the number of passageways and orifices provided may be equivalent to the number of sides forming the polygonal shaped body. More particularly, outlet 38 of passageway 26 may be positioned in the relative center of the respective side 30 of the polygonal body. The positioning of outlets 38 of passageways 26 may increase the flow of fluid along the surface of distal member 18 such that the entire or at least a substantial portion of polygonal body 28 may be subjected to the irrigation fluid flow provided by passageways 26.

Alternate configurations of distal member 18, in particular substantially polygonal shaped body 28, may be provided, such as shown, for example, in FIGS. 4A-4F. As previously discussed, distal member 18 may be configured to form a number of substantially polygonal shaped bodies 28. Although polygonal bodies traditionally include flat sides of equal length, various lengths may be used to create a polygonal shape having three sides or more. Moreover, a combination of flat sides and curved sides may be combined as discussed below to achieve various embodiments of the present invention which provides a substantially polygonal shaped body.

Figure 4A:
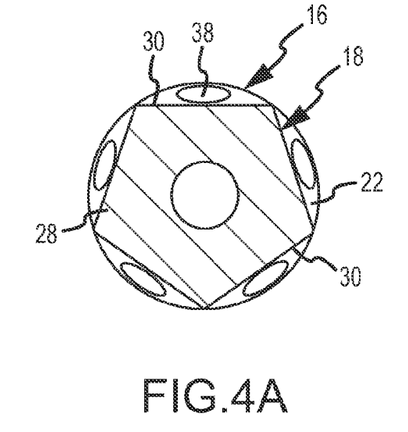
FIGS. 4A-4F are cross-sectional views of alternate embodiments of an irrigated ablation electrode assembly taken along line 4-4 as illustrated in FIGS. 2A and 2B.
Figure 4B:
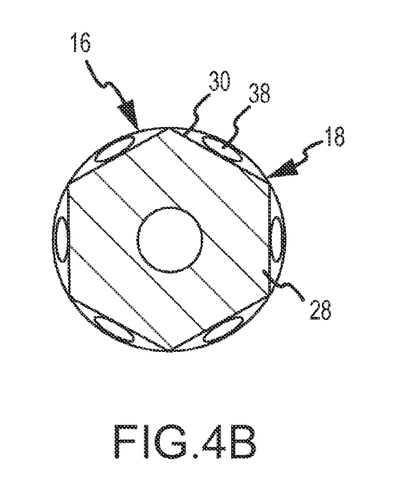
Figure 4C:
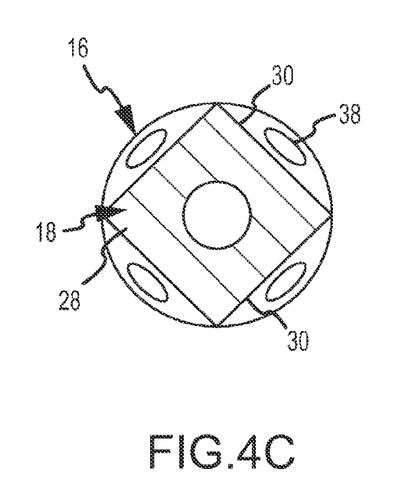
Figure 4D:
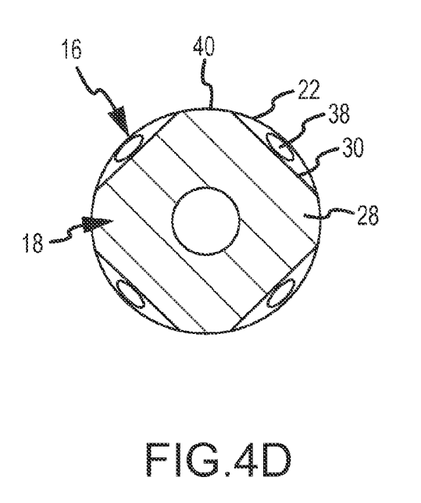
Figure 4E:
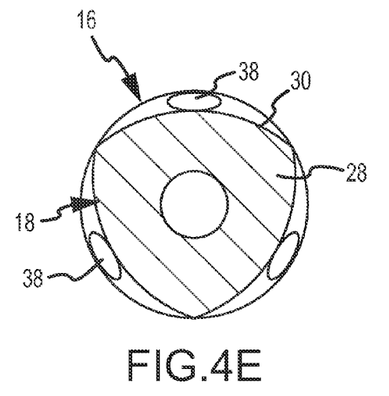
Figure 4F:
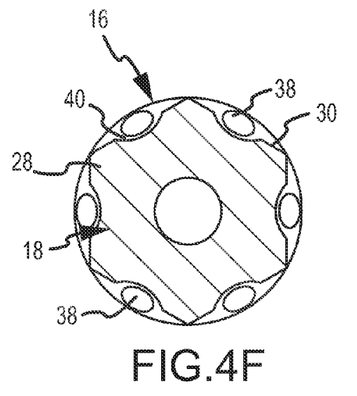

As shown in FIG. 4A, polygonal shaped body 28 includes a radial polygonal cross-section, which forms a pentagon, as previously described, having five sides 30 and including five passageways (not shown) leading to orifices 38 on the outer distal end surface 22 of proximal member 16. An alternate embodiment, as shown in FIG. 4B, provides polygonal shaped body 28 with six sides 30 forming a hexagon shaped body 28 of distal member 18. In accordance with an embodiment of the present invention, six passageways extending to orifices 38 are provided, one for each of the respective six sides 30 forming the hexagonal shaped body 28 of distal member 18. FIGS. 4C and 4D, each provide a square shaped body 28 including four passageways extending to orifices 38, one for each of the four respective sides 30. In comparison, FIG. 4D includes a curvature portion 40 between each pair of adjacent sides 30. In an embodiment, the radius of curvature of curved portion 40 may be equal to the radius of proximal member 16, therein providing a smooth surface transition in these locations between the outer body portion 20 of proximal member 16 and the polygonal shaped body 28 of distal member 18. FIG. 4E further illustrates a cross-section having a shaped body that includes a triangular-like shape having sides 30 with a slight curvature, which is convex as shown but may be concave in other embodiments. Various degrees of curvature may be provided or exhibited by the shaped electrode body 28 depending on the design of distal member 18. Moreover, FIG. 4F provides a substantially polygonal shaped body 28 wherein approximately six sides 30 are illustrated having a substantially hexagonal shaped body 28. Each side 30 further includes a concave curved portion 40 positioned between two flat portions, such that the curved portions 40 of sides 30 reflect the curvature of passageways 38. As can be seen, various configurations of distal member 18 may be provided including combinations of flat sides 30 and curved portions 40 to optimize the flow of fluid along body 28 of distal member 18.

Figure 5:
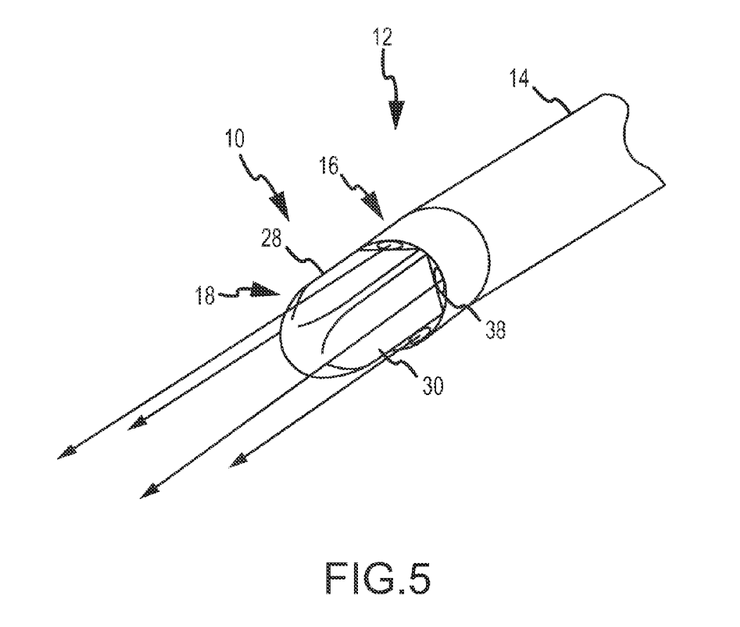
FIG. 5 illustrates the parallel flow of irrigation fluid in accordance with an embodiment of the present invention as shown in FIG. 1.

FIG. 5 illustrates the parallel irrigation flow of fluid from passageways 26 exiting proximal member 16 out orifices 38 and along sides 30 of body 28 of distal member 18. In an embodiment, the flow rate of fluid along distal member 18 is approximately 5 ml/min, although various flow rates may be maintained in order to sufficiently cool distal member 18 therein preventing the formation of thrombus or other related conditions.

Although a number of embodiments of this invention have been described above with a certain degree of particularity, those skilled in the art could make numerous alterations to the disclosed embodiments without departing from the spirit or scope of this invention. Other embodiments and uses of the devices and method of the present invention will be apparent to those skilled in the art from consideration of the specification and practice of the invention disclosed therein.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated ablation electrode assembly for use with an irrigated catheter device, comprising:
   a proximal portion and a distal portion disposed distal to the proximal portion, said proximal and distal portions having a longitudinal axis that extends from a proximal end of said proximal portion to a distal end of said distal portion,
   the distal portion defined by a substantially polygonal shaped body having sides forming a radial substantially polygonal cross-section; and
   the proximal portion having an outer body portion having an outer distal end surface, an inner cavity within the outer body portion, and a passageway for fluid that extends from the inner cavity to an orifice on the outer distal end surface of the proximal portion, the outer distal end surface being oriented toward the distal portion, the orifice being positioned in the relative center of a selected one of the sides of the polygonal body;
   the passageway being configured to direct fluid to flow onto the selected side substantially parallel to the longitudinal axis of the distal portion.

2. The electrode assembly of claim 1, wherein the proximal portion comprises a plurality of passageways disposed circumferentially about the outer body portion.

3. The electrode assembly of claim 2, wherein the number of passageways provided by the proximal portion are equal to the number of sides provided by the substantially polygonal shape body of the distal portion.

4. The electrode assembly of claim 3, wherein a respective orifice associated with each passageway is positioned in the relative center of a respective side of the polygonal shaped body.

5. The electrode assembly of claim 1, wherein the proximal portion and the distal portion form a single unitary electrode assembly.

6. The electrode assembly of claim 1, wherein the proximal portion and the distal portion are two separate components.

7. The electrode assembly of claim 1, wherein the proximal portion is a proximal member and the distal portion is a distal member.

8. The electrode assembly of claim 1, wherein the substantially polygonal cross-section of the distal portion includes three to six sides.

9. The electrode assembly of claim 8, wherein the sides of the substantially polygonal cross-section of the distal portion are equilateral.

10. The electrode assembly of claim 8, wherein the sides of the substantially polygonal cross-section of the distal portion are substantially straight.

11. The electrode assembly of claim 10, wherein the sides of the substantially polygonal cross-section of the distal portion further include a curved portion.

12. The electrode assembly of claim 11, wherein the curved portion of the sides is concave.

13. The electrode assembly of claim 1, wherein the passageway is positioned proximate to the sides of the distal portion.

14. The electrode assembly of claim 1, wherein the distal portion is comprised of an electrically conductive material.

15. The electrode assembly of claim 1, wherein the proximal portion is comprised of a thermally nonconductive material.

16. The electrode assembly of claim 1, wherein the flow of fluid from the passageway out of the orifice is parallel to at least a portion of the sides of the distal portion.

17. The electrode assembly of claim 1, wherein the distal portion further includes a rounded distal end.

18. The electrode assembly of claim 1, wherein a thermal sensor is disposed within the distal portion.

19. The electrode assembly of claim 1, wherein a line extending through the passageway forms an acute angle with a longitudinal axis of the electrode assembly.

20. The electrode assembly of claim 18, wherein said acute angle ranges from approximately 5 degrees to approximately 25 degrees.

21. The electrode assembly of claim 1, wherein the passageway is curved.

22. The electrode assembly of claim 1, wherein the passageway is straight.

23. An irrigated catheter assembly comprising:
   a catheter including a catheter shaft having a fluid lumen; and
   an irrigated ablation electrode assembly including
   a proximal portion and a distal portion disposed distal to the proximal portion, said proximal and distal portions having a longitudinal axis that extends from a proximal end of said proximal portion to a distal end of said distal portion,
   the distal portion defined by a substantially polygonal shaped body having sides forming a radial substantially polygonal cross-section; and
   the proximal portion having an outer body portion having an outer distal end surface, an inner cavity within the outer body portion, and a passageway for fluid that extends from the inner cavity to an orifice in the outer distal end surface of the proximal portion, the outer distal end surface being oriented toward the distal portion, the orifice being positioned in the relative center of a selected one of the sides of the polygonal body;
   the passageway being configured to direct fluid to flow onto the selected side substantially parallel to the longitudinal axis of the distal portion.

24. The irrigated catheter assembly of claim 23, wherein the proximal portion of the electrode assembly comprises a plurality of passageways disposed circumferentially about the outer body portion.

25. The irrigated catheter assembly of claim 24, wherein the number of passageways provided by the proximal portion are equal to the number of sides provided by the substantially polygonal shaped body of the distal portion.

26. The irrigated catheter assembly of claim 25, wherein a respective orifice associated with each passageway is positioned in the relative center of a respective side of the polygonal shaped body.

27. The irrigated catheter assembly of claim 23, wherein the substantially polygonal cross-section of the distal portion includes three to six sides.

* * * * *